United States Patent
Nishiura et al.

(10) Patent No.: US 8,986,856 B2
(45) Date of Patent: Mar. 24, 2015

(54) IRIDIUM COMPLEX AND ORGANIC LIGHT-EMITTING ELEMENT INCLUDING THE SAME

(75) Inventors: Chiaki Nishiura, Kawasaki (JP); Shigemoto Abe, Yokohama (JP); Masashi Hashimoto, Tokyo (JP); Hiroya Nitta, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 471 days.

(21) Appl. No.: 13/513,850

(22) PCT Filed: Nov. 26, 2010

(86) PCT No.: PCT/JP2010/071755
§ 371 (c)(1), (2), (4) Date: Jun. 4, 2012

(87) PCT Pub. No.: WO2011/070992
PCT Pub. Date: Jun. 16, 2011

(65) Prior Publication Data
US 2012/0248427 A1    Oct. 4, 2012

(30) Foreign Application Priority Data
Dec. 8, 2009   (JP) .................. 2009-278969

(51) Int. Cl.
*H01L 51/54* (2006.01)
*C09K 11/06* (2006.01)
*C07F 15/00* (2006.01)
*H01L 51/00* (2006.01)
*H01L 51/50* (2006.01)
*H05B 33/14* (2006.01)

(52) U.S. Cl.
CPC ............. *C07F 15/0033* (2013.01); *C09K 11/06* (2013.01); *H01L 51/0085* (2013.01); *H01L 51/5016* (2013.01); *H05B 33/14* (2013.01); *C09K 2211/1007* (2013.01); *C09K 2211/1044* (2013.01); *C09K 2211/185* (2013.01); *H01L 51/001* (2013.01); *Y10S 428/917* (2013.01)
USPC .... 428/690; 428/917; 313/504; 257/E51.044; 548/103; 544/225

(58) Field of Classification Search
None
See application file for complete search history.

(56) References Cited

FOREIGN PATENT DOCUMENTS

| | | |
|---|---|---|
| JP | 2005-53912 A | 3/2005 |
| JP | 2006-513278 A | 4/2006 |
| JP | 2007-208102 A | 8/2007 |
| WO | 2004016711 A1 | 2/2004 |

*Primary Examiner* — Marie R. Yamnitzky
(74) *Attorney, Agent, or Firm* — Canon U.S.A., Inc. IP Division

(57) ABSTRACT

The present invention provides a novel iridium complex and an organic light-emitting element including the same. The novel iridium complex includes phenylpyrazole as a ligand and has a basic skeleton in which a pyrimidine ring is bonded to a phenyl ring.

11 Claims, 3 Drawing Sheets

IRIDIUM COMPLEX AND ORGANIC LIGHT-EMITTING ELEMENT INCLUDING THE SAME

TECHNICAL FIELD

The present invention relates to a novel iridium complex and an organic light-emitting element including the same.

BACKGROUND ART

Organic light-emitting elements are being actively developed. Novel phosphorescent materials are being developed for developing organic light-emitting elements. Patent Literature 1 describes an iridium complex represented by the following structural formula.

[Chem. 1]

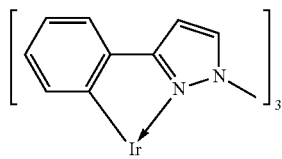

CITATION LIST

Patent Literature

[PTL 1] Japanese Patent Laid-Open No. 2005-053912

Although the structural formula described in Patent Literature 1 is disclosed, light emission characteristics are not specifically described. In addition, compounds of the above structural formual have a weak lgand field and cannot be expected to have excellent light emission characteristics as blue light-emitting materials.

The present invention provides an iridium complex which emits blue phosphorescence and has excellent light emission characteristics. Also the present invention provides an organic light-emitting element including the iridium complex and having excellent external quantum yield.

SUMMARY OF INVENTION

The present invention provides an iridium complex represented by the following general formula (1):

[Chem. 2]

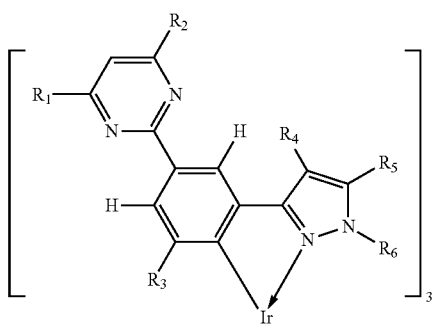

In the formula (1), $R_1$ and $R_2$ are each independently selected from a tertiary butyl group, an adamantyl group, and a bicyclooctyl group. $R_3$ is any one of a hydrogen atom, a halogen atom, and a cyano group. $R_4$ and $R_5$ are each independently selected from a hydrogen atom, a halogen atom, a cyano group, an alkyl group, an alkoxy group, and an amino group. $R_6$ is an alkyl group.

DESCRIPTION OF EMBODIMENTS

Figure 1:
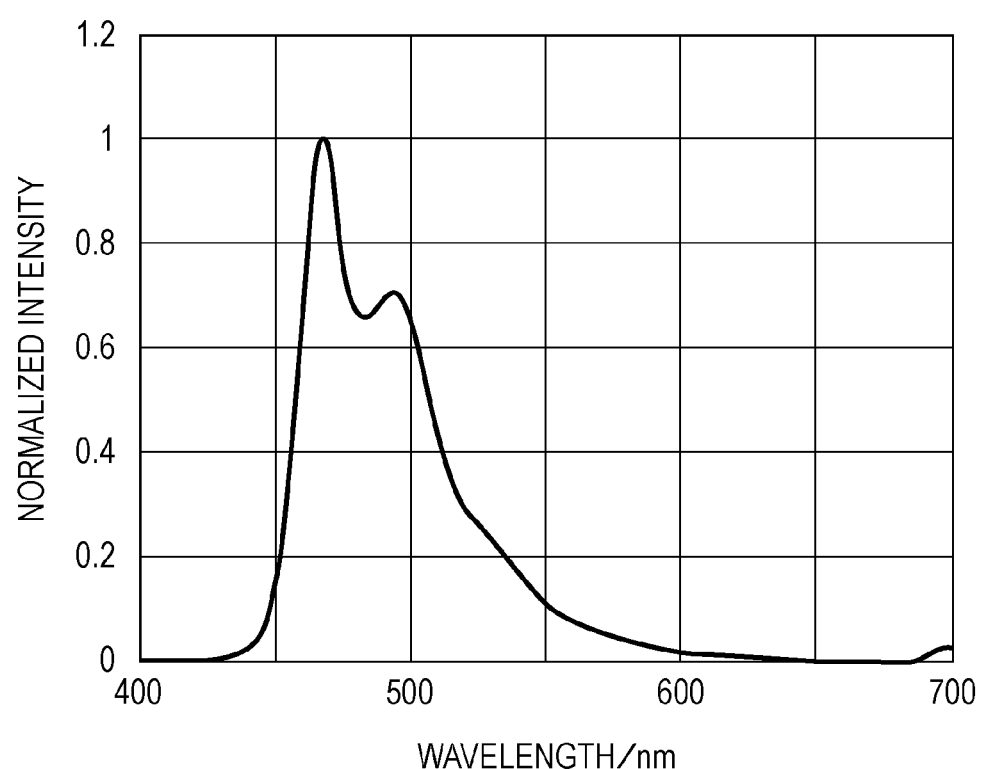
FIG. 1 is a diagram showing an emission spectrum of compound 1-1 according to the present invention.

An iridium complex according to the present invention is represented by the following general formula (1):

[Chem. 3]

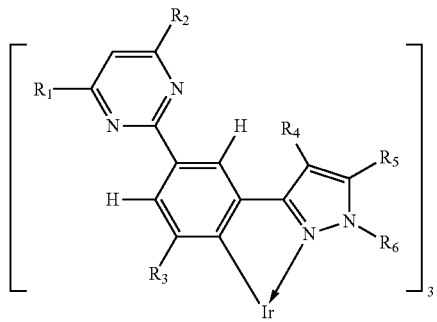

$R_1$ and $R_2$ are each independently selected from a tertiary butyl group, an adamantyl group, and a bicyclooctyl group. $R_3$ is any one of a hydrogen atom, a halogen atom, and a cyano group. $R_4$ and $R_5$ are each independently selected from a hydrogen atom, a halogen atom, a cyano group, an alkyl group, an alkoxy group, and an amino group. $R_6$ is an alkyl group.

A halogen atom as $R_3$ is, for example, a fluorine atom, a chlorine atom, a bromine atom, or an iodine atom. Substituents $R_4$ and $R_5$ may be the same or different from each other. A halogen atom as each of $R_4$ and $R_5$ is, for example, a fluorine atom, a chlorine atom, a bromine atom, or a iodine atom. An alkyl group as each of $R_4$ and $R_5$ is, for example, a methyl group, an ethyl group, an isopropyl group, a tertiary butyl group, or a adamantyl group. An amino group as each of $R_4$ and $R_5$ is, for example, a dimethylamino group or a diisopropylamino group. An alkyl group as $R_6$ is, for example, a methyl group, an ethyl group, an isopropyl group, a tertiary butyl group, or an adamantyl group.

As shown in the general formula (1), an iridium complex represented by the general formula (1) according to the present invention has a ligand with a skeleton in which a pyrimidine ring, a phenyl ring, and a pyrazole ring, excluding $R_1$ to $R_6$ and H, are bonded at specified positions. This skeleton is referred to as a "ligand main skeleton of general formula (1)" hereinafter.

Blue phosphorescence emission of the iridium complex of the present invention is exhibited by virtue of the ligand main skeleton of general formula (1).

Conceivable ligand structures including a pyrimidine ring, a phenyl ring, and a pyrazole ring include four structures A to D described below. However, the structure C, i.e., the ligand main skeleton of general formula (1), is excellent as a basic skeleton of light-emitting materials in a blue region.

[Chem. 4]

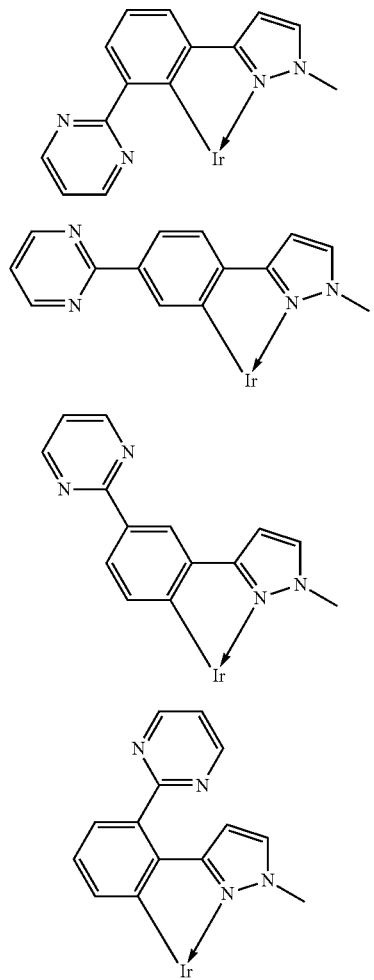

In order to achieve excellent light emission characteristics in the blue region, it is necessary to use a ligand capable of forming a strong ligand field.

In order to increase the ligand field, it is important to increase Π back donation from iridium as a central metal to the ligand.

The term "Π back donation" represents that electrons are donated from a central metal to a ligand in a complex.

The inventors have found that two requirements below are important for effectively producing the Π back donation due to the electron-withdrawing property of a pyrimidine ring. The structures A to D have iridium, a pyrimidine ring, a phenyl ring, and a pyrazole ring.

Requirement 1: A substitution position of a pyrimidine ring bonded to a phenyl ring bonded to iridium is the ortho or para position on the phenyl ring with respect to iridium.

Requirement 2: A pyrimidine ring and a phenyl ring are coplanar to each other.

Structure B contains a pyrimidine ring at the meta position on a phenyl ring with respect to iridium and does not satisfy requirement 1.

Structures A and D each contain a phenyl ring and a pyrimidine ring which cannot maintain a planar structure in three dimensions due to steric repulsion, at an adjacent position to a bonding position of a pyrimidine ring, of iridium atom in structure A and of a pyrazole ring in structure D. Therefore, structures A and D do not satisfy requirement 2.

Therefore, only structure C satisfies the two requirements and is excellent as a light-emitting material in the blue region, which has the ligand main skeleton of general formula (1).

Further, two H atoms possessed by a phenyl ring, i.e., two H atoms represented by the general formula (1), are important for maintaining planarity of a pyrimidine ring and a phenyl ring.

The values of dihedral angle between a pyrimidine ring and a phenyl ring determined by molecular orbital calculation are shown in a table below.

[Chem. 5]

| Structural formula | ![pyrimidine-phenyl] | ![difluoro] | ![dimethyl] |
|---|---|---|---|
| Dihedral angle between two rings | 0.00° | 47.9° | 54.4° |

Therefore, from the viewpoint of maintaining planarity of a pyrimidine ring and a phenyl ring, it is important that two ortho positions on a phenyl ring with respect to a pyrimidine ring are hydrogen atoms.

A dihedral angle was calculated using a commercial software for electronic state calculation, Gaussian 03* Revision D.01. Geometry optimization calculation was performed, using the software, for a ground state of a phenyl group with fluorine and a methyl group introduced at the 2 and 6 positions.

In this case, density functional theory was used as a quantum chemical calculation method, and B3LYP was used as a functional. In Gaussian 30, Revision D.01, 6-31G* was used as a basis function.

* Gaussian 03, Revision D.01,

M. J. Frisch, G. W. Trucks, H. B. Schlegel, G. E. Scuseria,

M. A. Robb, J. R. Cheeseman, J. A. Montgomery, Jr., T. Vreven,

K. N. Kudin, J. C. Burant, J. M. Millam, S. S. Iyengar, J. Tomasi,

V. Barone, B. Mennucci, M. Cossi, G. Scalmani, N. Rega,
G. A. Petersson, H. Nakatsuji, M. Hada, M. Ehara, K. Toyota,
R. Fukuda, J. Hasegawa, M. Ishida, T. Nakajima, Y. Honda, O. Kitao,
H. Nakai, M. Klene, X. Li, J. E. Knox, H. P. Hratchian, J. B. Cross,
V. Bakken, C. Adamo, J. Jaramillo, R. Gomperts, R. E. Stratmann,
O. Yazyev, A. J. Austin, R. Cammi, C. Pomelli, J. W. Ochterski,
P. Y. Ayala, K. Morokuma, G. A. Voth, P. Salvador, J. J. Dannenberg,
V. G. Zakrzewski, S. Dapprich, A. D. Daniels, M. C. Strain, O. Farkas, D. K. Malick, A. D. Rabuck, K. Raghavachari,
J. B. Foresman, J. V. Ortiz, Q. Cui, A. G. Baboul, S. Clifford,
J. Cioslowski, B. B. Stefanov, G. Liu, A. Liashenko, P. Piskorz,
I. Komaromi, R. L. Martin, D. J. Fox, T. Keith, M. A. Al-Laham,
C. Y. Peng, A. Nanayakkara, M. Challacombe, P. M. W. Gill, B. Johnson, W. Chen, M. W. Wong, C. Gonzalez, and J. A. Pople,
Gaussian, Inc., Wallingford Conn., 2004.

Although $R_1$ and $R_2$ in the general formula (1) are each independently selected, they are the same substituent from the viewpoint of simplicity of material synthesis.

The substituents $R_1$ and $R_2$ are provided for protecting the pyrimidine ring. Therefore, it is important that the substituents are bulky substituents. Specifically, as described above, $R_1$ and $R_2$ are each any one of a tertiary butyl group, an adamantyl group, and a bicyclooctyl group. For example, a tertiary butyl group can be used for avoiding an excessive increase in molecular weight of the iridium complex.

By introducing an alkyl group with a large excluded volume, at least any one of the followings can be expected.

1. A high purity and high yield can be achieved.
2. Incorporation of ionic impurities due to a lone electron pair is suppressed by suppressing the coordinative ability of a nitrogen atom, thereby improving the life of an organic light-emitting element.
3. Concentration quenching of a light-emitting material can be suppressed by suppressing intermolecular interaction. The concentration quenching represents a phenomenon that luminous efficiency is decreased at a high concentration.

In the general formula (1), $R_6$ is an alkyl group. This indicates that $R_6$ is not a hydrogen atom. When $R_6$ is a hydrogen atom, a by-product is undesirably produced due to a tautomer of hydrogen in synthesis of the complex. In addition, from the viewpoint of synthesis yield of the complex, a substituent having a small excluded volume can be used. Specifically, a methyl group can be used.

The iridium complex according to the present invention can be used for a blue phosphorescent material. Therefore, the iridium complex can be used as a light-emitting material of an organic light-emitting element. The light-emitting element is described later. In addition, the iridium complex of the present invention has a band gap sufficient for use as a host material of a light-emitting layer of an organic light-emitting element which emits green or red light.

Specific examples of the iridium complex according to the present invention are given below.

[Chem. 6]

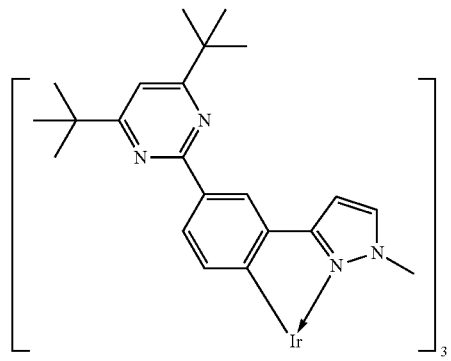

Exemplified Compound 1-1

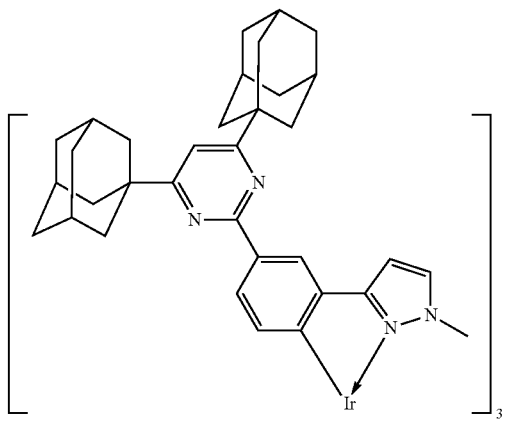

Exemplified Compound 1-2

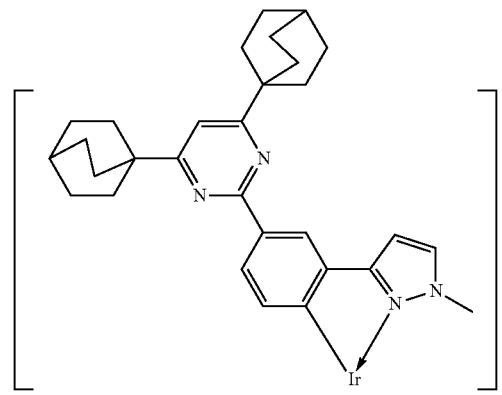

Exemplified Compound 1-3

Exemplified Compound 2-1
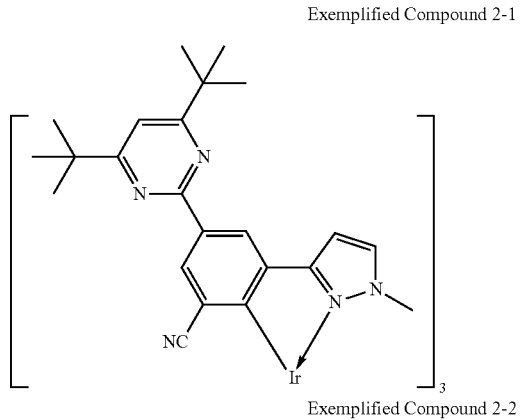
Exemplified Compound 2-2
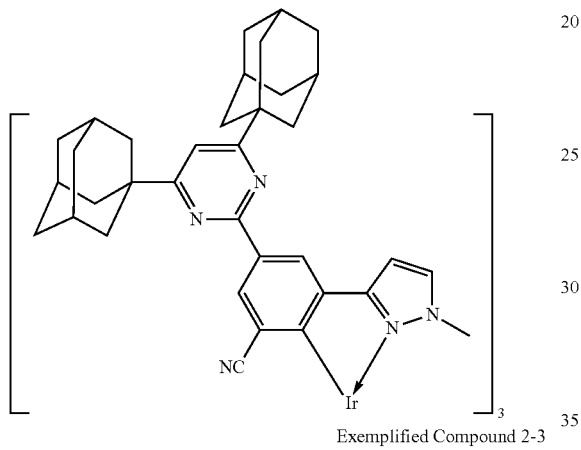
Exemplified Compound 2-3
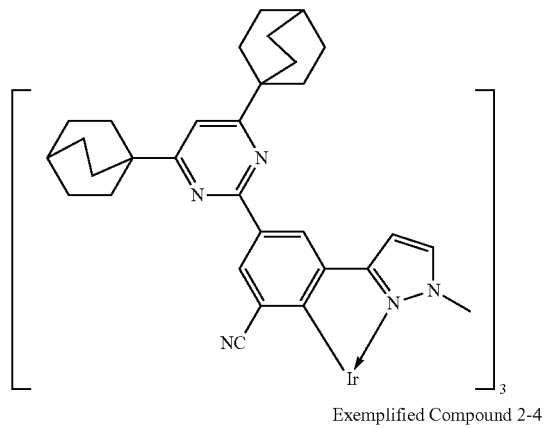
Exemplified Compound 2-4
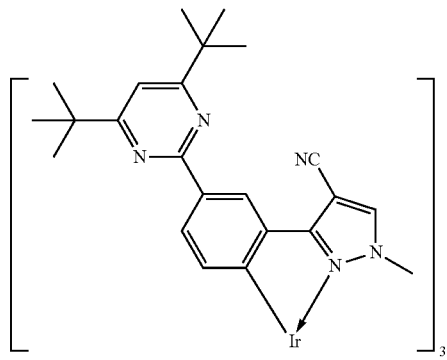
Exemplified Compound 2-5
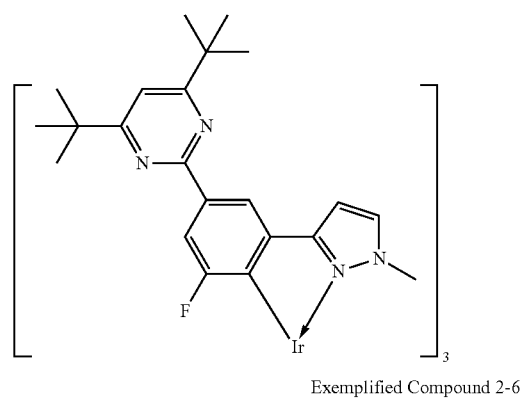
Exemplified Compound 2-6
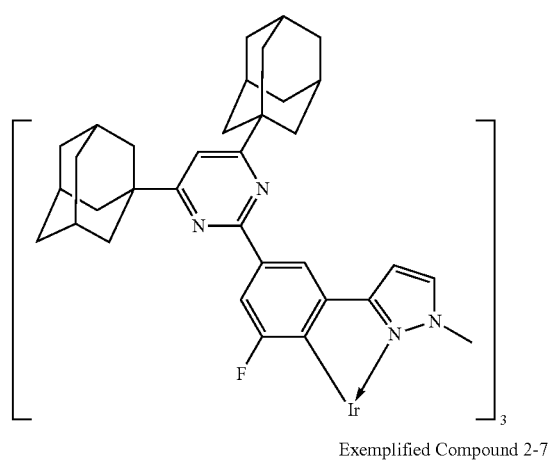
Exemplified Compound 2-7
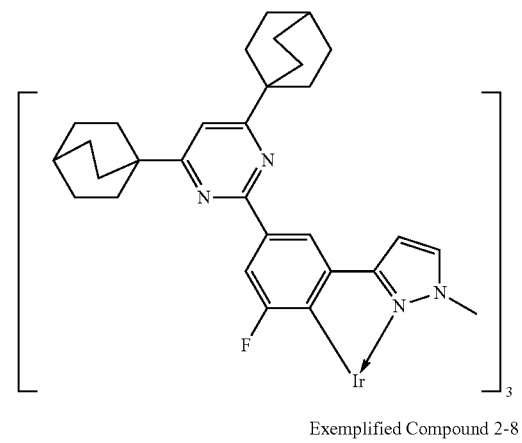
Exemplified Compound 2-8
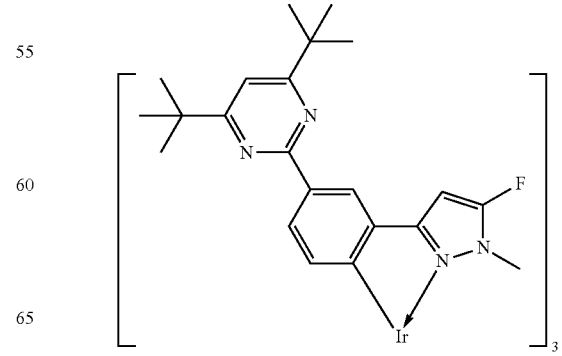

Exemplified Compound 3-1
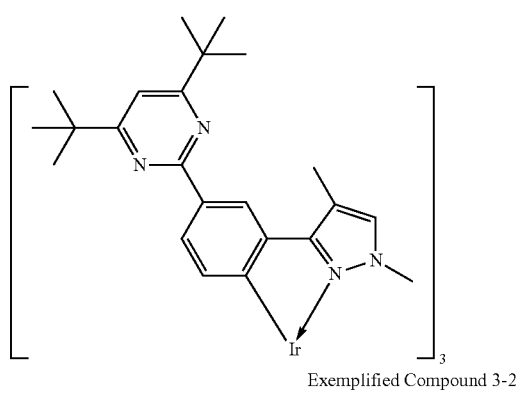
Exemplified Compound 3-2
Exemplified Compound 3-3
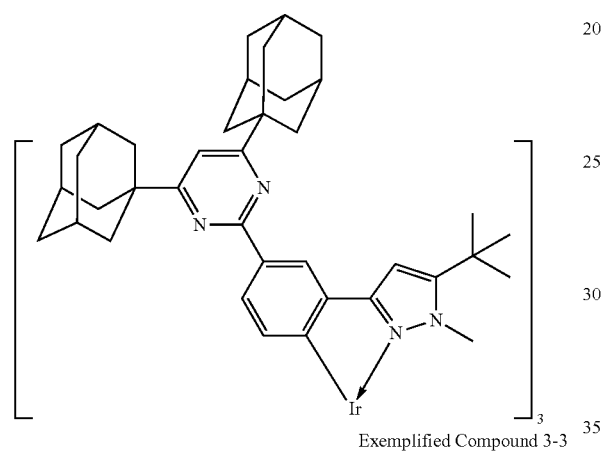
Exemplified Compound 3-4
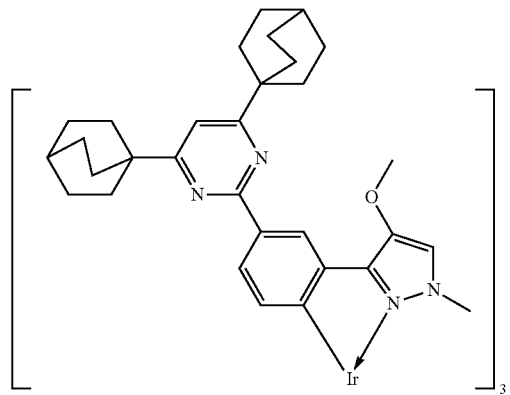
Exemplified Compound 3-5
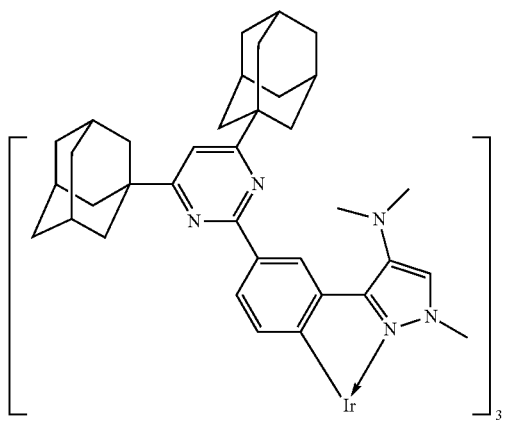
Exemplified Compound 3-6
[Chem. 9]
Exemplified Compound 4-1
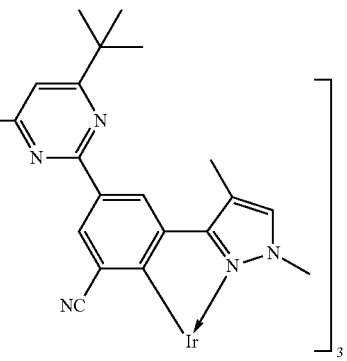

Exemplified Compound 4-2

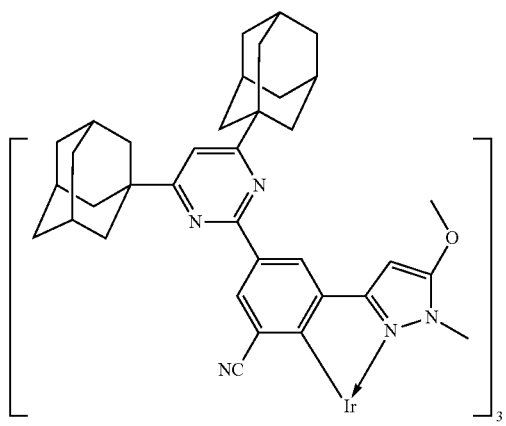

Exemplified Compound 4-3

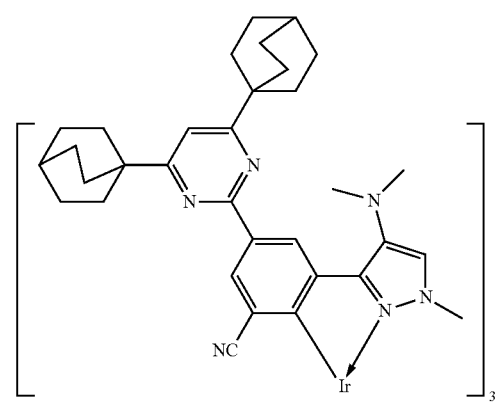

Exemplified Compound 4-4

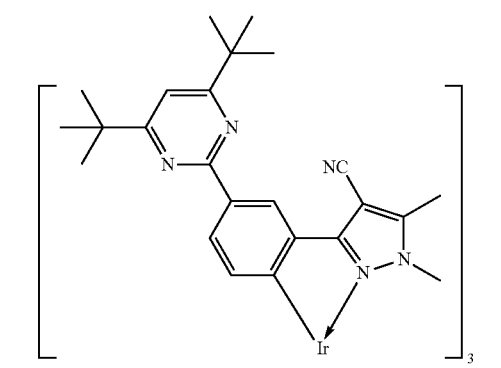

Exemplified Compound 4-5

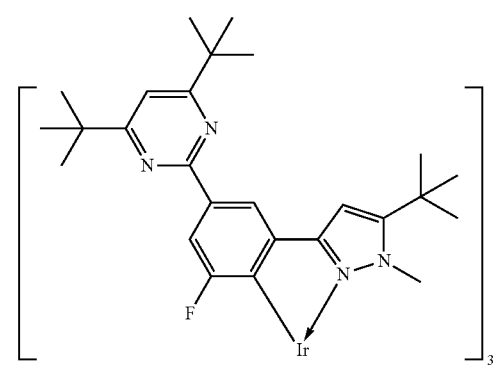

Exemplified Compound 4-6

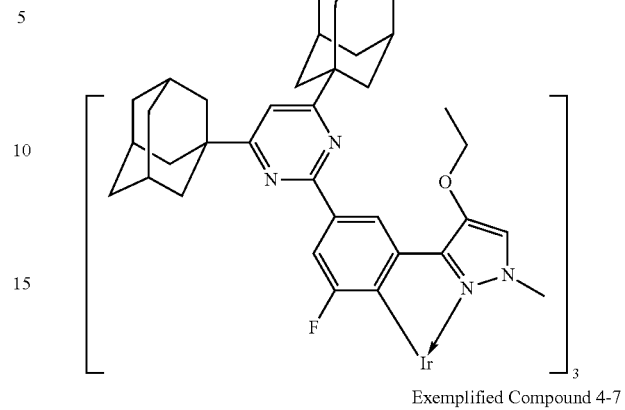

Exemplified Compound 4-7

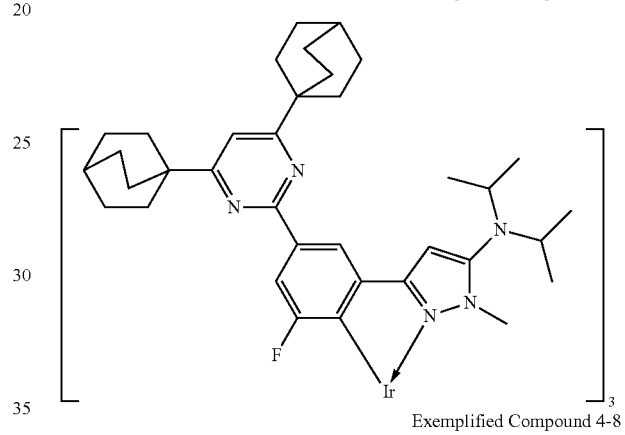

Exemplified Compound 4-8

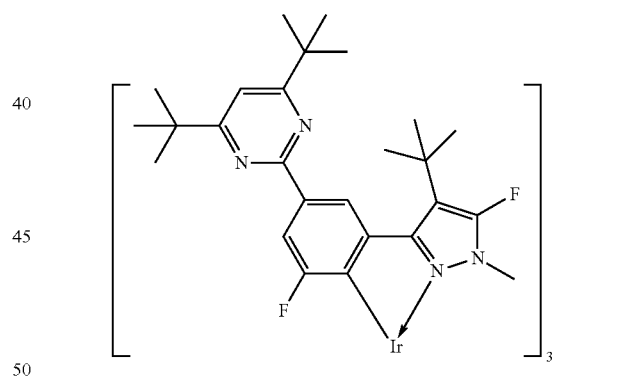

The iridium complex according to the present invention is useful as a material for an organic light-emitting element. Also, the iridium complex according to the present invention can be used as a guest material or a host material of a light-emitting layer of an organic light-emitting element. The organic light-emitting element includes a pair of opposing electrodes and a light-emitting layer disposed between the electrodes. The organic light-emitting layer may include a layer other than the light-emitting layer. The iridium complex according to the present invention can be properly used for a layer other than the light-emitting layer, i.e., any one of an electron transport layer, an electron injection layer, a hole transport layer, a hole injection layer, and an exciton/hole blocking layer.

As for the host material and the guest material, herein, the host material is a compound at the highest weight ratio among the compounds constituting the light-emitting layer, and the guest material is a compound at a lower weight ratio than that of the host material among the compounds constituting the light-emitting layer.

The iridium complex according to the present invention can be used as a guest material of a light-emitting layer of an organic light-emitting element. In particular, the iridium complex can be used as a guest material of a blue light-emitting element.

An emission wavelength can be changed by introducing a substituent into the basic skeleton of the iridium complex according to the present invention.

When the iridium complex according to the present invention is used as a guest material of a light-emitting layer, a material having a higher LUMO level than the iridium complex, in other words, a host material in a level close to the vacuum level, can be used as a host material. This is because since the iridium complex according to the present invention has a low LUMO level, electrons supplied to the light-emitting layer, i.e., the host material, can be more satisfactorily received from the host material. The LUMO level is an abbreviation of the lowest unoccupied molecular orbital level. In addition, a HOMO level is an abbreviation of the highest occupied molecular orbital level. The host material and the guest material are further described later.

Next, synthesis examples of the iridium complex according to the present invention are described, starting from a synthesis example of a ligand.

(Description of Synthesis Route)

First, a synthesis example of a ligand is described.

<Synthesis Example of Ligand>

Scheme 1

[Chem. 10]

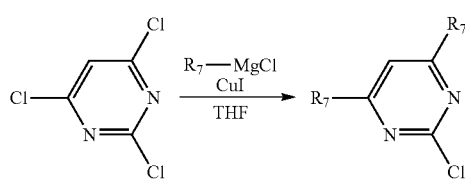

In this scheme, various substituents can be introduced by changing $R_7$-MgCl as a Grignard reagent.

Scheme 2

[Chem. 11]

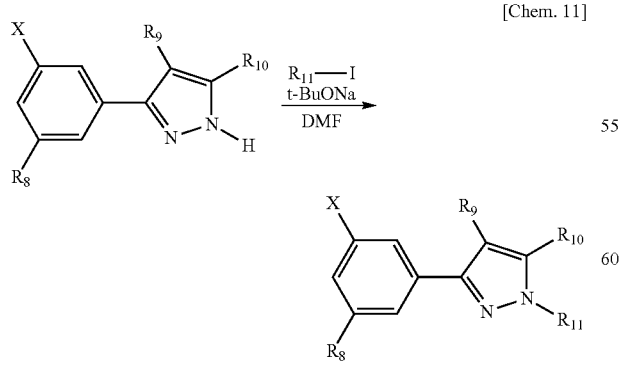

In this scheme, various ligands can be synthesized using, as a raw material, halogen materials containing substituents introduced as $R_8$ to $R_{10}$. In addition, various substituents can be introduced by changing a halide $R_{11}$—I.

Scheme 3

[Chem. 12]

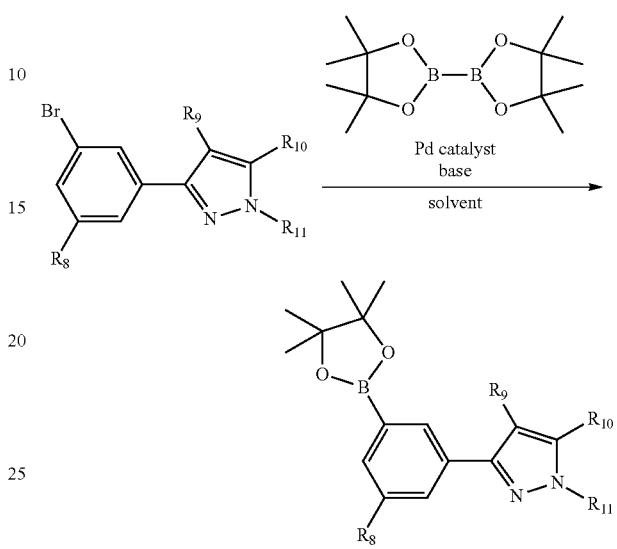

In this scheme, a halogen material used as a raw material is not limited to a bromine material and may be, for example, an iodide material or triflate. In addition, a product may be boronic acid or the like.

Scheme 4

[Chem. 13]

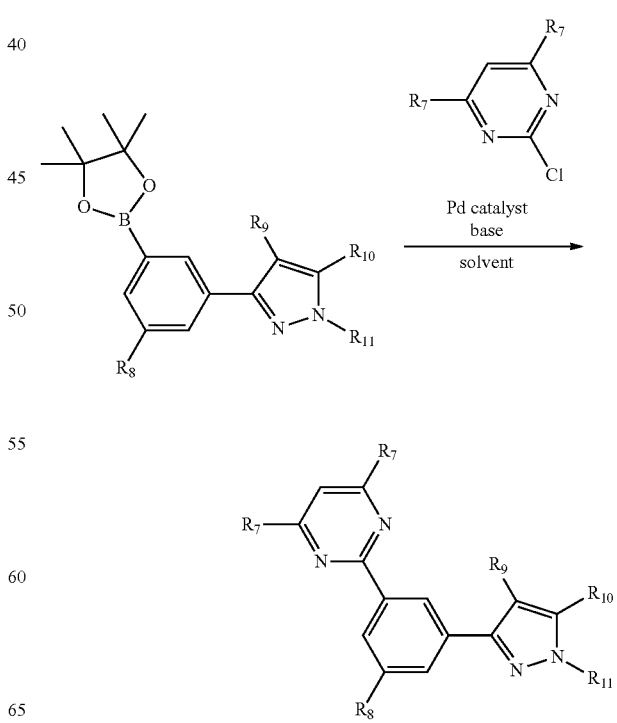

Various ligands can be synthesized by selecting halogenated pyrimidine synthesized in Scheme 1 and a boronic acid derivative with 3-phenylpyrazole as a basic skeleton synthesized in Scheme 3.

Next, synthesis examples of the iridium complex are described.

<Synthesis Examples of Iridium Complex>

Here, two examples of synthesis of the iridium complex are described.

<One-Step Synthesis Example>

A one-step synthesis example using iridium trisacetylacetonate complex as a raw material is described.

Scheme 5

[Chem. 14]

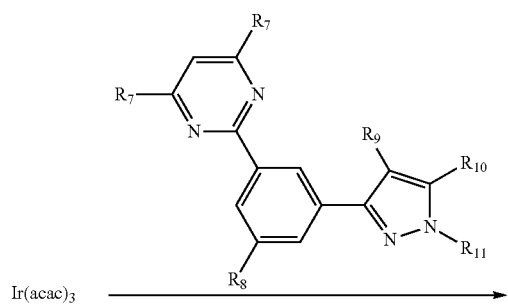

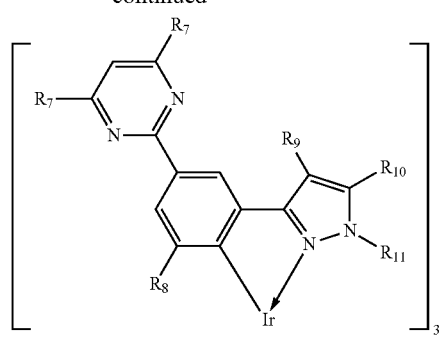

In this scheme, a solvent is not particularly specified, but a protonic solvent having a high boiling point, such as ethylene glycol, glycerol, or the like, can be used.

<Three-Step Synthesis Example>

Next, a three-step synthesis example using iridium trichloride as a raw material is described.

Scheme 6

[Chem. 15]

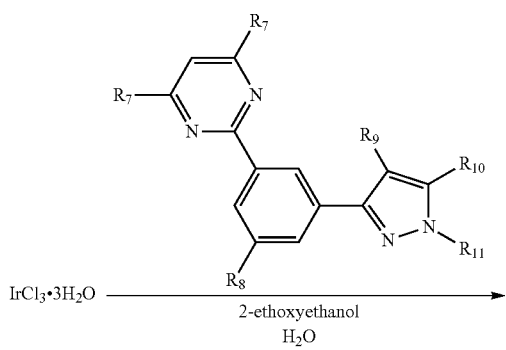

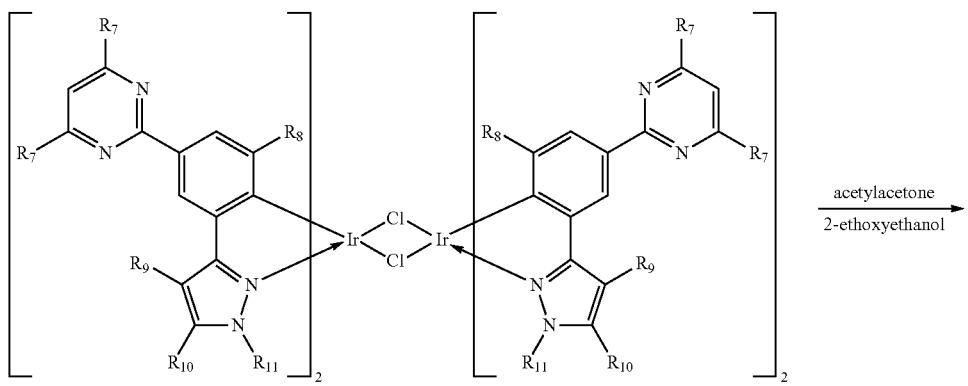

-continued

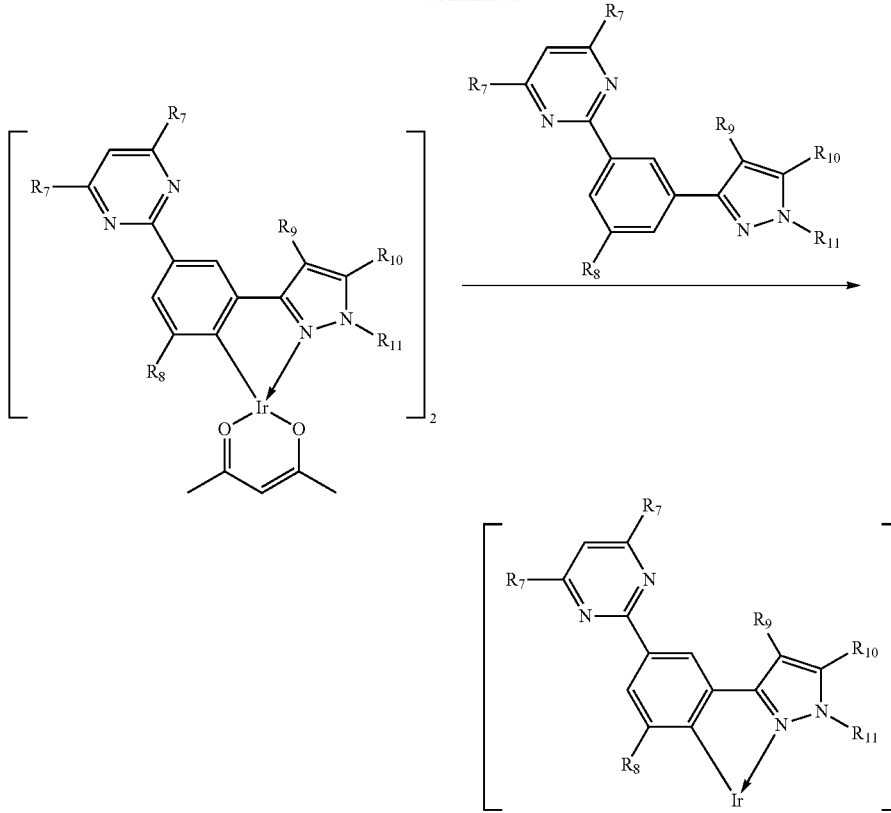

A reaction in the third step in this scheme may be performed using, for example, ethylene glycol or glycerol, or may be solvent-less reaction.

Next, an organic light-emitting element according to the present invention is described.

An organic light-emitting element according to the present invention includes a pair of electrodes and an organic compound layer disposed between the pair of electrodes. The pair of electrodes include, for example, an anode and a cathode. An electric field in a forward direction necessary for emitting light or an electric field in a reverse direction may be applied to the pair of electrodes.

The organic compound layer includes the iridium complex according to the present invention.

Other than this organic compound layer, the organic light-emitting element may contain an organic compound layer.

The organic light-emitting element according to the present invention includes a light-emitting layer disposed between the anode and the cathode. The light-emitting layer may be an organic compound layer containing the iridium complex according to the present invention or may include the organic compound layer containing the iridium complex according to the present invention and another organic compound layer. The organic compound layer containing the iridium complex according to the present invention may be or not be the light-emitting layer. For example, at least any one of a hole injection layer, a hole transport layer, a hole/exciton blocking layer, an electron transport layer, and an electron injection layer may contain the iridium complex according to the present invention.

A combination of the organic compound layer containing the iridium complex according to the present invention and another organic layer may be appropriately selected. A plurality of other organic compound layers may be provided.

A layer structure between the anode and the cathode of the organic light-emitting element according to an embodiment of the present invention is described.

A first layer structure is formed by laminating the anode, the light-emitting layer, and the cathode.

A second layer structure includes a laminate of the anode, the hole transport layer, and the electron transport layer. In this case, when light emission is observed between the hole transport layer and the electron transport layer, the light-emitting layer may include the hole transport layer and the electron transport layer.

A third layer structure includes a laminate of the anode, the hole transport layer, the light-emitting layer, the electron transport layer, and the cathode.

A fourth layer structure includes a laminate of the anode, the hole injection layer, the hole transport layer, the light-emitting layer, the electron transport layer, and the cathode.

A fifth layer structure includes a laminate of the anode, the hole transport layer, the light-emitting layer, the hole/exciton blocking layer, the electron transport layer, and the cathode.

The iridium complex according to the present invention can be used for any of the layers in these first to fifth layer structures.

An organic compound which constitutes the hole injection layer or the hole transport layer is a compound having high hole mobility. In this case, the organic compound may be a low-molecular compound or a high-molecular compound. Examples of such a compound include triarylamine derivatives, phenylenediamine derivatives, stilbene derivatives, phthalocyanine derivatives, polyphyrin derivatives, poly(vinylcarbazole), poly(thiophene), and other conductive polymers. Examples are shown below.

[Chem. 16]

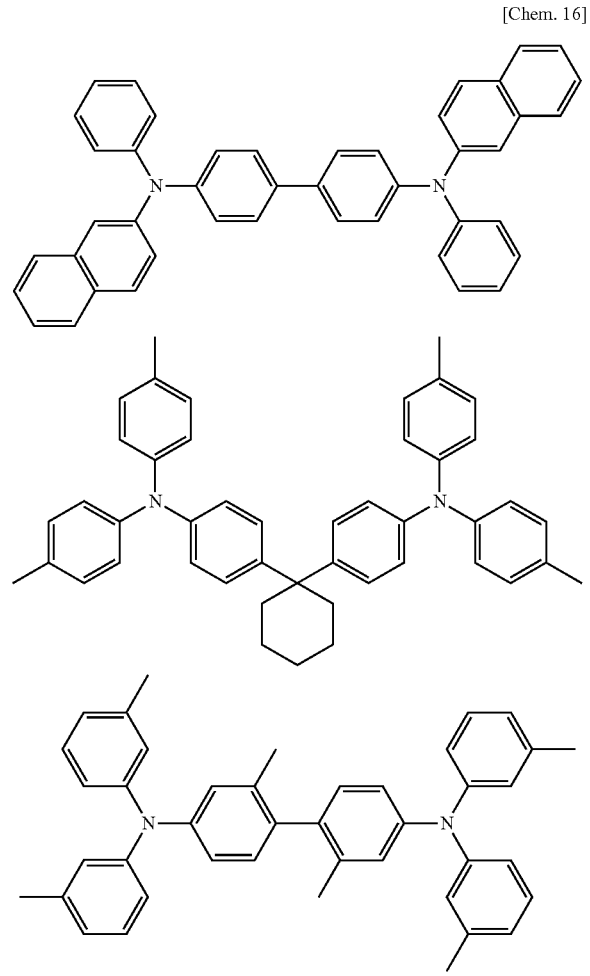

An organic compound which constitutes the electron injection layer or the electron transport layer is selected in consideration of balance with the hole mobility of the compound contained in the hole injection layer or the hole transport layer. Examples of the compound include oxadiazole derivatives, oxazole derivatives, pyrazine derivatives, triazole derivatives, triazine derivatives, quinoline derivatives, quinoxaline derivatives, phenanthroline derivatives, organic aluminum complexes, and the like. Examples are shown below.

[Chem. 17]

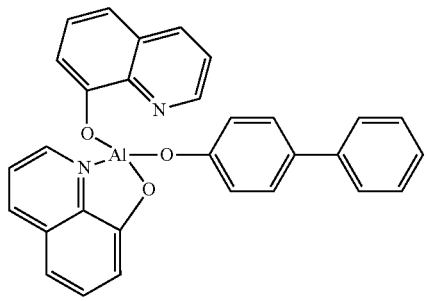

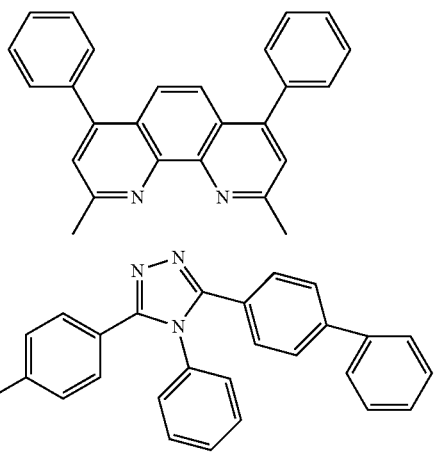

The light-emitting layer may be composed of only a single organic compound or a plurality types of organic compounds. When the light-emitting layer contains a plurality types of organic compounds, the plurality types of organic compounds include a host material and the guest material. The host material is a main component of the light-emitting layer and has a higher weight ratio than the guest material. The amount of the guest material as a sub-component is 0.01 wt % or more and 20 wt % or less and more preferably 0.5 wt % or more and 10 wt % or less of the total weight of the light-emitting layer. The guest material is a light-emitting material that determines the luminescent color of the organic light-emitting element. When the light-emitting layer contains a plurality types of organic compounds, the plurality types of organic compounds may include an emission assist material and a charge injection material besides the host material and the guest material.

The host material may be a material in which carriers of both holes and electrons sufficiently move. In addition, a material having a higher triplet lowest excitation energy level T1 than that of the light-emitting material can be used in order that excitons produced in the light-emitting layer are efficiently utilized for light emission. Examples of the host material include fused ring compounds (e.g., fluorene derivatives, naphthalene derivatives, carbazole derivatives, quinoxaline derivatives, and quinoline derivatives), organic aluminum complexes such as tris(8-quinolinolate)aluminum and the like, organic zinc complexes, and polymer derivatives such as triphenylamine derivatives, poly(fluorene) derivatives, poly(phenylene) derivatives, and the like. Examples are shown below.

[Chem. 18]

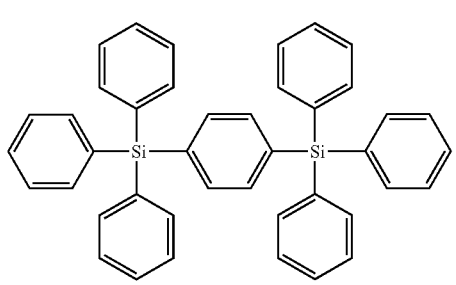

-continued

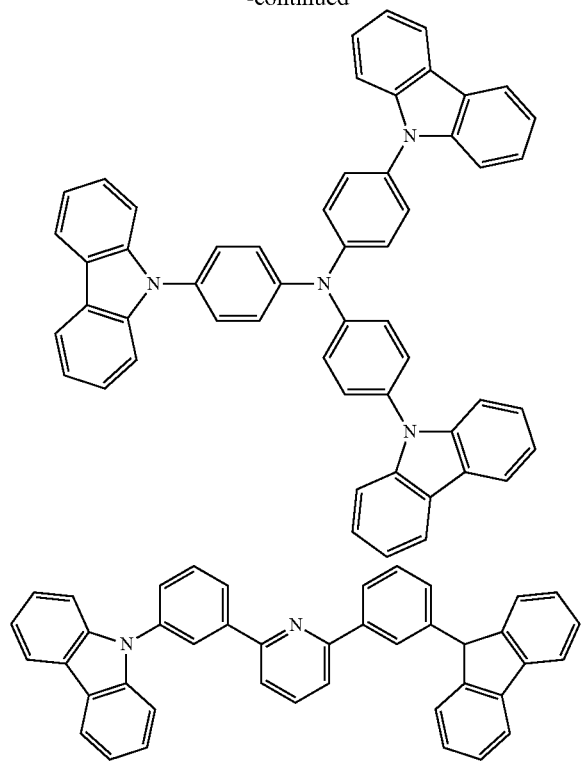

A material having as large work function as possible can be used for the anode. Examples of such a material include elemental metals such as gold, platinum, silver, copper, nickel, palladium, cobalt, selenium, vanadium, tungsten, and the like, alloys thereof, metal oxides such as tin oxide, zinc oxide, indium oxide, indium tin oxide (ITO), indium zinc oxide, and the like. Also, conductive polymers such as polyaniline, polypyrrole, polythiophene, and the like can be used. These electrode materials may be used alone or in combination of two or more. In addition, the anode may have a single layer structure or a multilayer structure.

A material having small work function can be used for the cathode. Examples of such a material include elemental metals such as alkali metals, e.g., lithium and the like, alkaline-earth metals, e.g., calcium and the like, aluminum, titanium, manganese, silver, lead, chromium, and the like. Also, alloys of a combination of these elemental metals can be used. For example, magnesium-silver, aluminum-lithium, aluminum-magnesium, and the like can be used. Also, metal oxides such as indium tin oxide (ITO) and the like can be used. These electrode materials may be used alone or in combination of two or more. In addition, the cathode may have a single layer structure or a multilayer structure.

A layer containing the iridium complex according to the present invention and a layer containing another organic compound are formed by a method described below. A thin film is formed by a vacuum evaporation method, an ionized evaporation method, sputtering, plasma coating, or a coating method of applying a solution in a proper solvent (for example, spin coating, dipping, casting, LB method, an ink jet method, or the like). When a layer is formed by the vacuum evaporation method, the solution coating method, or the like, crystallization little occurs, and temporal stability is excellent. When a film is formed by the coating method, the film can be formed by combining a proper binder resin.

Examples of the binder resin are given below. Examples include a polyvinyl carbazole resin, polycarbonate resin, a polyester resin, an ABS resin, an acrylic resin, a polyimide resin, a phenol resin, an epoxy resin, a silicone resin, and a urea resin.

These binder resins may be used alone as a homopolymer or a copolymer or used as a mixture of two or more. Further, if required, known additives such as a plasticizer, an antioxidant, an ultraviolet absorber, and the like may be used in combination.

The organic light-emitting element according to the present invention can be used in a display device and an illuminating device. Besides these, the organic light-emitting element can be used for an exposure light source of an electrophotographic image forming apparatus, a back light of a liquid crystal display device, and the like.

The display device includes the organic light-emitting element according to the present invention provided in a display portion. The display device is capable of display by virtue of the organic light-emitting element.

In addition, the display portion includes a pixel which may include the organic light-emitting element according to the present invention. The display device can be used as an image display device of PC or the like.

The display device can also be used in a display portion of an imaging apparatus such as a digital camera, a digital video camera, or the like. The imaging apparatus includes the display portion and an imaging portion having an imaging optical system for taking images.

The display device may include an image input portion and a display portion. The image input portion serves as the imaging optical system, a light-receiving unit of CCD or the like, a unit which receives a memory card or the like, a scanner, or the like. Besides the above-described digital camera and digital video camera, the apparatus including the organic light-emitting element according to the present invention provided in the display portion may be, for example, a multifunction-type image forming apparatus having a scanner function and an image output function. The multifunction-type image forming apparatus may be an ink jet image forming apparatus or an electrophotographic image forming apparatus.

Next, a display device using the organic light-emitting element according to the present invention is described.

Figure 3:
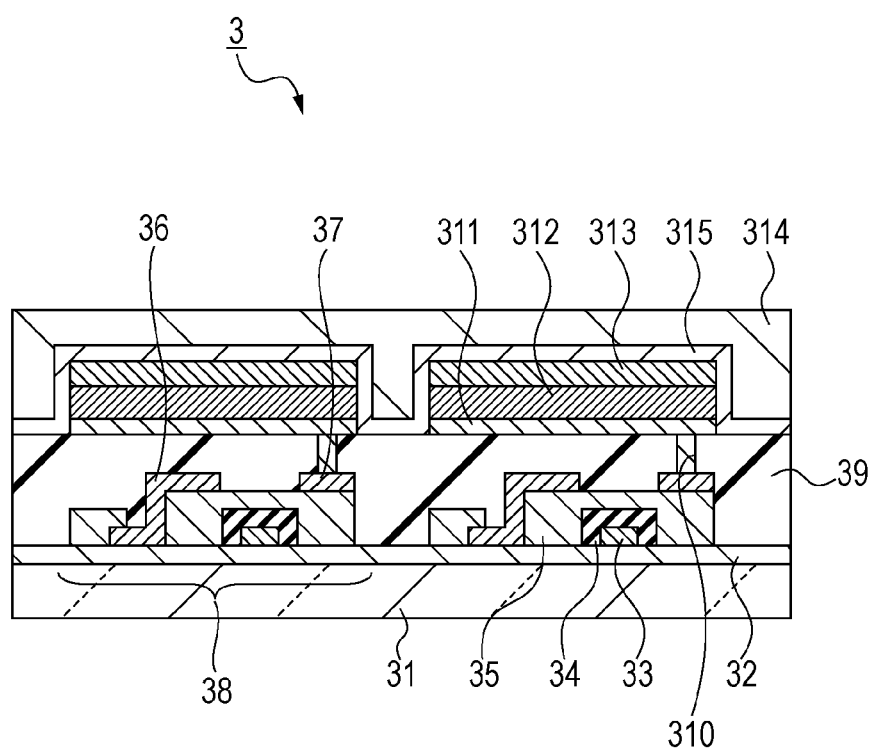
FIG. 3 is a schematic sectional view showing an organic light-emitting element and a switching element connected to the organic light-emitting element.

FIG. 3 is a schematic sectional view of a display device which shows an organic light-emitting element serving as a pixel and a switching element connected to the organic light-emitting element. In this figure, the switching element is a TFT element. Other than this, the switching element may be a MIM element.

A display device 3 includes a substrate 31 of glass or the like and a moisture proofing film 32 provided thereon to protect a TFT element or an organic compound layer. In addition, reference numeral 33 denotes a gate electrode of a metal such as Cr or the like. Reference numeral 34 denotes a gate insulting film, and reference numeral 35 denotes a semiconductor layer.

A TFT element 38 includes the semiconductor film 35, a drain electrode 36, and a source electrode 37. An insulating film 39 is provided over the TFT element 38. An anode 311 of the organic light-emitting element is connected to the source electrode 37 through a contact hole (through hole) 310.

In FIG. 3, a plurality of organic compound layers 312 is shown as a single layer for the sake of convenience. Further, a first protective layer 314 and a second protective layer 315 are provided on a cathode 313 in order to suppress deterioration of the organic light-emitting element.

The emission luminance of the organic light-emitting element is controlled by the TFT element. A plurality of organic light-emitting elements are provided in a plane so that an image can be displayed with emission luminance of each of the elements.

EXAMPLES

Examples are described below.

Example 1

Synthesis of Exemplified Example 1-1

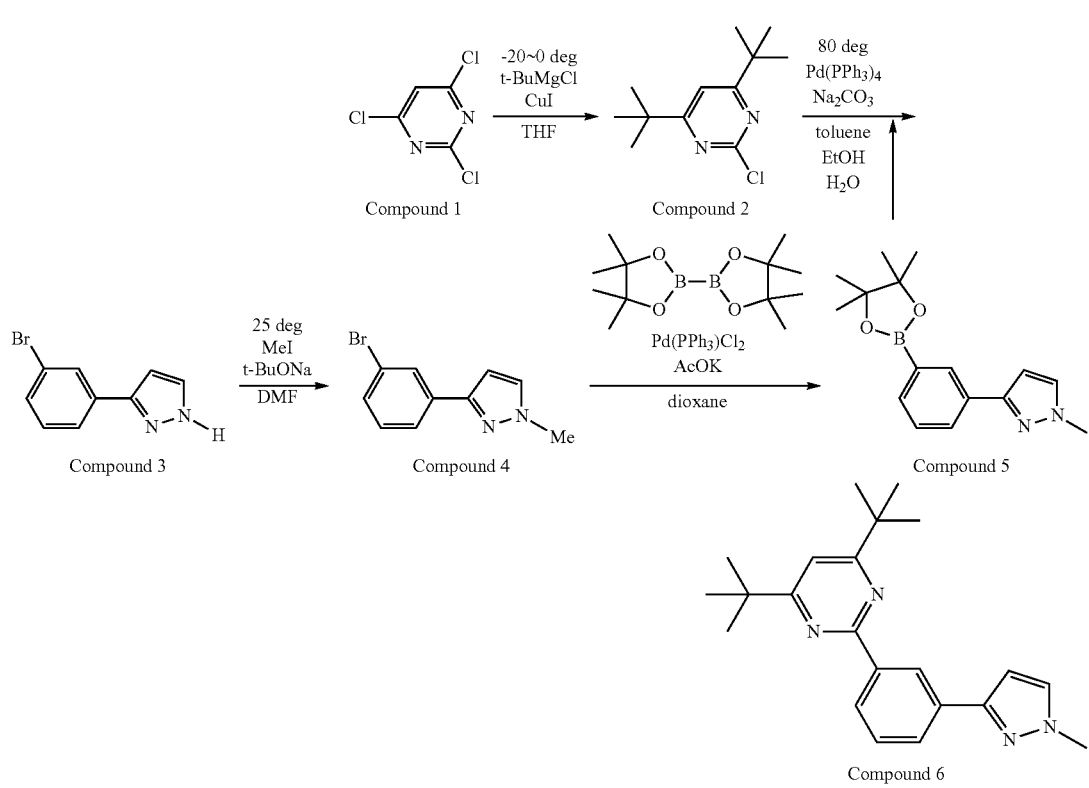

[Chem. 19]

Synthesis of Intermediate Compound 2

In a 500 ml three-necked flask, 20.0 g (109 mmol) of compound 1, 1.04 g (5.45 mmol) of copper iodide, and 100 ml of THF were placed, followed by cooling to −20° C. After bubbling with nitrogen for 10 minutes, 120 ml (241 mmol) of a 2 mol/L tert-butylmagnesium chloride THF solution was added dropwise at a rate such that the reaction solution did not exceed 0° C. After the addition, the solution was stirred at room temperature for 24 hours. The loss of the raw materials and production of a new compound were confirmed by gas chromatography. An organic phase was recovered by three times of separation using a tert-butyl methyl ether/an aqueous saturated ammonium chloride solution and then separation with tert-butyl methyl ether/water. The organic phase was dried over magnesium sulfate, concentrated, and then purified by silica gel column chromatography (developing solvent; heptane:toluene=6:1). A target substance was concentrated to produce 19.5 g (85.6 mmol) of compound 2 (yield 80.0%). One proton was attributed by $^1$H-NMR (CDCl$_3$: 7.20 (s, 1H)).

A peak was observed at m/z=183 in GS-MS (gas chromatography direct-coupled to mass spectrometry) to confirm the target compound.

Synthesis of Intermediate Compound 4

In a 300 ml eggplant-type flask, 7.00 g (31.4 mmol) of compound 3, 3.30 g (34.5 mmol) of sodium tert-butoxide, and 100 ml of DMF were placed. Then, 2.15 ml (34.5 mmol) of idomethane was added dropwise to the resultant mixture, followed by stirring at room temperature for 24 hours. The loss of the raw materials and production of a new compound were confirmed by TLC (Thin Layer Chromatography). The reaction solution was concentrated, and an organic phase was recovered by three times of separation with toluene/water. The organic phase was dried over magnesium sulfate, concentrated, and then purified by silica gel column chromatography (developing solvent toluene:heptane:ethyl acetate=10:10:1). A target substance was concentrated to produce 5.21 g (22.0 mmol) of compound 4 (yield 70.0%). Nine protons were attributed by $^1$H-NMR (CDCl$_3$: 7.95 (s, 1H), 7.71 ppm (d, 1H), 7.42–7.39 ppm (m, 2H), 7.26 ppm (t, 1H), 6.53 ppm (d, 1H), 3.96 ppm (s, 3H)). A peak was observed at m/z=236 in GS-MS (gas chromatography direct-coupled to mass spectrometry) to confirm the target compound.

Synthesis of Intermediate Compound 5

In a 500 ml eggplant-type flask, 5.00 g (21.1 mmol) of compound 4, 5.89 g (23.2 mmol) of bis(pinacolato)diboron, and 300 ml of dioxane were placed, followed by bubbling with nitrogen for 15 minutes. Then, 296 mg (0.422 mmol) of bis(triphenylphosphine)palladium(II) dichloride and 6.20 g (63.0 mmol) of potassium acetate were added to the resultant mixture, followed by stirring under heating at 80° C. for 8 hours. The loss of the raw materials and production of a new compound were confirmed by TLC (Thin Layer Chromatography). An organic phase was recovered by two times of separation with toluene/water. The organic phase was dried over magnesium sulfate, concentrated, and then purified by silica gel column chromatography (developing solvent; toluene:heptane:ethyl acetate=1:4:1). A target substance was concentrated to produce 4.20 g (14.8 mmol) of compound 5 (yield 75.0%). Twenty seven protons were attributed by $^1$H-NMR to confirm the target compound (CDCl$_3$: 8.19 (s, 1H), 7.94 ppm (d, 1H), 7.74 ppm (d, 1H), 7.40 ppm (t, 1H), 7.37 ppm (d, 1H), 6.60 ppm (d, 1H), 3.95 ppm (s, 3H), 1.38–1.32 ppm (m, 18H)).

Synthesis of Intermediate Compound 6

In a 500 ml eggplant-type flask, 2.63 g (11.6 mmol) of compound 2, 3.00 g (10.6 mmol) of compound 5, 150 ml of toluene, 75 ml of ethanol, and 150 ml of water were placed, followed by bubbling with nitrogen for 15 minutes. Then, 366 mg (0.317 mmol) of tetrakis(triphenylphosphine) palladium (0) and 31 g (292 mmol) of potassium carbonate were added to the resultant mixture, followed by stirring under heating at 80° C. for 8 hours. The loss of the raw materials and production of a new compound were confirmed by TLC (Thin Layer Chromatography). An organic phase was recovered by two times of separation with toluene/water. The organic phase was dried over magnesium sulfate, concentrated, and then purified by silica gel column chromatography (developing solvent; toluene:heptane:ethyl acetate=1:3:1). A target substance was concentrated to produce 3.40 g (9.75 mmol) of compound 6 (yield 92.0%). Twenty seven protons were attributed by $^1$H-NMR to confirm the target compound (CDCl$_3$: 8.91 (s, 1H), 8.51 ppm (d, 1H), 7.95 ppm (d, 1H), 7.50 ppm (t, 1H), 7.42 ppm (d, 1H), 7.19 ppm (s, 1H), 6.67 ppm (d, 1H), 3.96 ppm (s, 3H), 1.40-1.35 ppm (m, 18H)).

[Chem. 20]

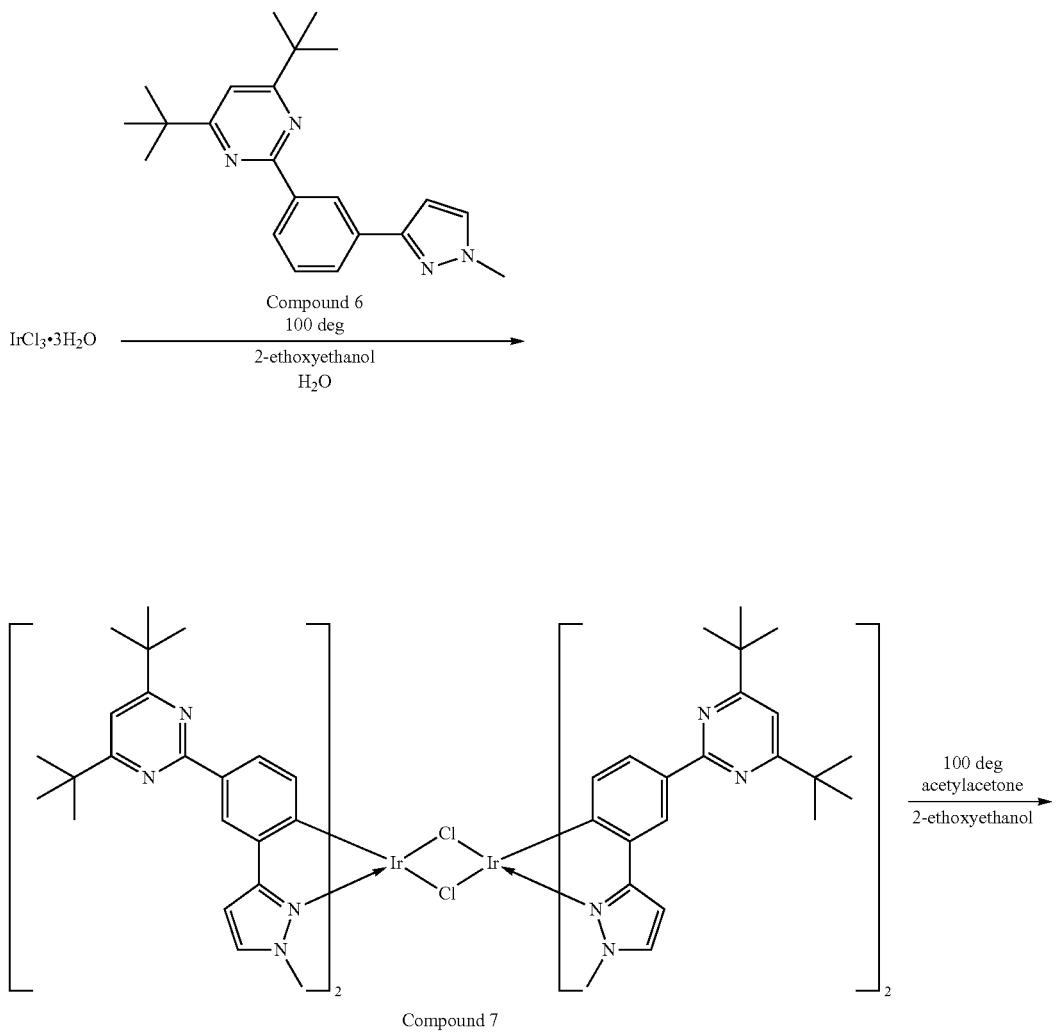

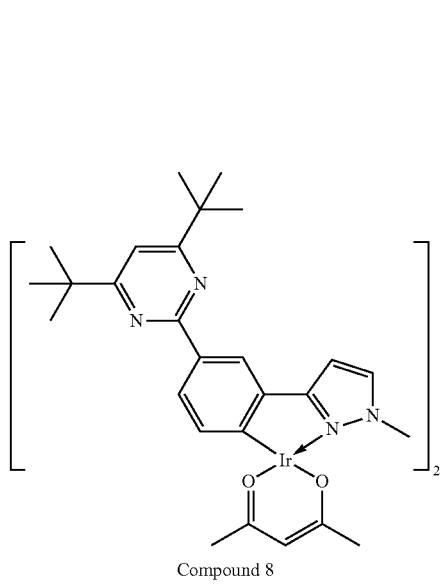

Compound 8

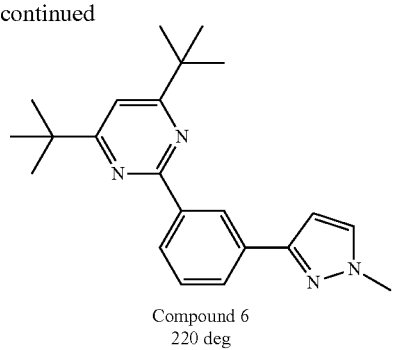

Compound 6
220 deg

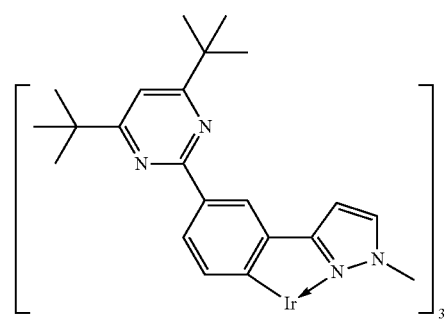

Exemplified Compound 1-1

Synthesis of Intermediate Compound 7

In a 100 ml eggplant-type flask, 1.00 g (2.87 mmol) of compound 6, 460 mg (1.30 mol) of iridium trichloride trihydrate, 20 ml of 2-ethoxyethanol, and 7 ml of water were placed. After bubbling with nitrogen for 10 minutes, the resulting mixture was stirred under heating at 100° C. for 12 hours. Then, a small amount of sample was collected from the reaction solution and analyzed by $^1$H-NMR to confirm the production of a new compound. After the reaction solution was returned to room temperature, precipitates were filtered off. The precipitates were washed with 20 ml of methanol and filtered off to produce 779 mg (0.422 mmol) of compound 7 (yield 68.0%). One hundred and eight protons were attributed by $^1$H-NMR to confirm the target compound (CDCl$_3$: 8.42 (s, 4H), 7.73 ppm (d, 4H), 7.58 ppm (d, 4H), 7.00 ppm (s, 4H), 6.82 ppm (d, 4H), 6.02 ppm (d, 4H), 3.84 ppm (s, 12H), 1.38-1.32 ppm (m, 72H)).

Synthesis of Intermediate Compound 8

In a 100 ml eggplant-type flask, 500 mg (0.271 mmol) of compound 7, 271 μl (2.71 mmol) of acetylacetone, 144 mg (1.36 mmol) of sodium carbonate, and 15 ml of 2-ethoxyethanol were placed. The resultant mixture was stirred under heating at 100° C. for 12 hours. Then, a small amount of sample was collected from the reaction solution and analyzed by $^1$H-NMR to confirm the production of a new compound. After the reaction solution was returned to room temperature, 30 ml of water was added to the solution and stirred for 10 minutes, and precipitates were filtered off. The precipitates were washed with 20 ml of methanol and filtered off to produce 446 mg (0.452 mmol) of compound 8 (yield 83.0%). Fifty five protons were attributed by $^1$H-NMR to confirm the target compound (CDCl$_3$: 8.46 (s, 2H), 7.81 ppm (d, 2H), 7.49 ppm (d, 2H), 7.00 ppm (s, 2H), 6.72 ppm (d, 2H), 6.24 ppm (d, 2H), 5.33 ppm (s, 1H), 3.84 ppm (s, 6H), 1.38-1.32 ppm (m, 36H)).

Synthesis of Exemplified Compound 1-1

In a 10 ml eggplant-type flask, 200 mg (0.203 mmol) of compound 8 and 1.00 g (2.87 mmol) of compound 6 were placed. The resultant mixture was stirred under heating at 220° C. for 24 hours. The loss of the raw materials and production of a new compound were confirmed by TLC. The reaction solution was washed with 30 ml of toluene and filtered. The filtered residue was dissolved in DMF and purified by alumina column chromatography (developing solvent DMF). Further, the product was recrystallized with DMF to produce 37.5 mg (0.0406 mmol) of exemplified compound 1-1 (yield 20.0%). Eighty one protons were attributed by $^1$H-NMR (CDCl$_3$: 8.56 (s, 3H), 7.94 ppm (dd, 3H), 7.21 ppm (d, 3H), 7.02 ppm (s, 3H), 6.87 ppm (d, 3H), 6.63 ppm (d, 3H), 3.23 ppm (s, 9H), 1.37-1.32 ppm (m, 54H)). A peak was observed at m/z=1234 in MALDI-TOF (Matrix-Assisted Laser Desorption/Ionization Time-Of-Flight Mass Spectrometry) to confirm the target compound.

An emission spectrum of the exemplified compound 1-1 was measured at room temperature. As measurement conditions, a $1\times10^{-5}$ mol/l toluene solution was measured using Hitachi F-4500 at an excitation wavelength of 350 nm. The exemplified compound 1-1 showed a spectrum having a maximum wavelength of 466 nm at room temperature. The half-width of the emission spectrum was 50 nm, and chromaticity was x=0.14 and y=0.25 in the CIE standard color system.

Figure 2:
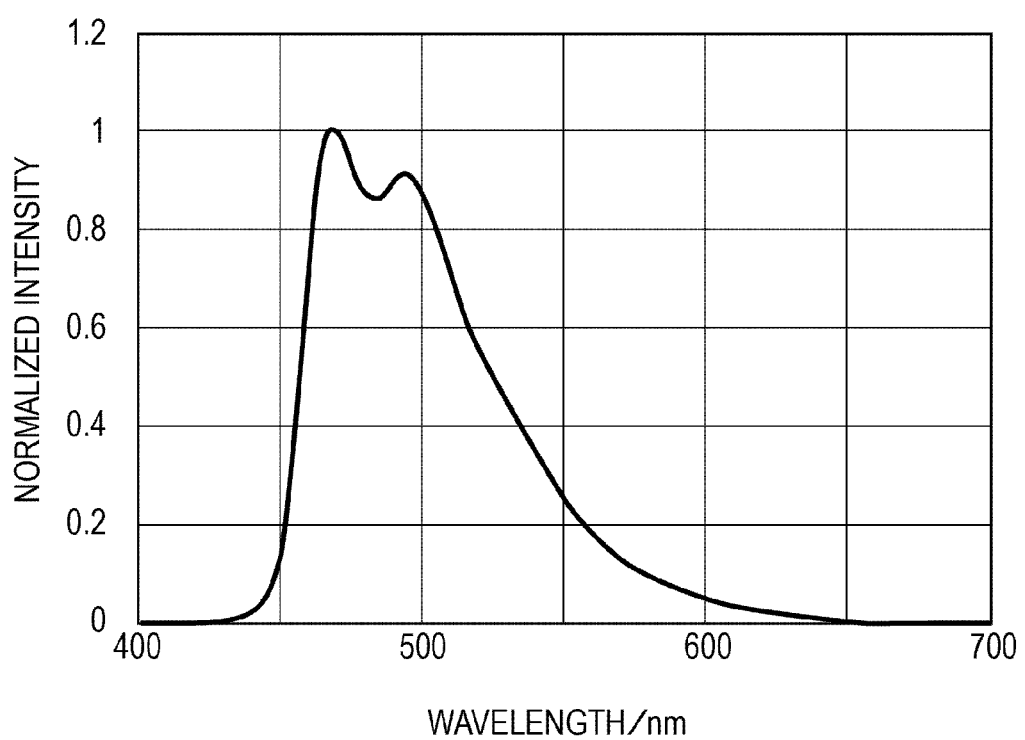
FIG. 2 is a diagram showing an emission spectrum of compound 9 of a comparative example.

In addition, for comparison, FIG. 2 shows a spectrum, at room temperature, of compound 9 which was an iridium complex used as a general blue light-emitting material and represented by the following structural formula:

[Chem. 21]

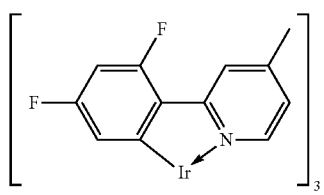

Compound 9

This compound has a maximum wavelength of 468 nm. The half-width of the emission spectrum was 66 nm, and chromaticity was x=0.15 and y=0.34 in the CIE standard color system.

According to the above-described measurement, the exemplified compound 1-1 has a half-width value 16 nm narrower than that of compound 9.

In addition, the exemplified compound 1-1 has chromaticity closer to blue (x=0.14 and y=0.08 in the CIE standard color system) in the NTSC system than the compound 9 and is thus excellent as a blue light-emitting material for display. Namely, the compound of the present invention has an emission spectrum having a narrow half-width and is excellent as a blue light-emitting material.

A glass substrate on which indium tin oxide (ITO) was deposited to a thickness of 120 nm by sputtering to form an anode was used as a transparent conductive support substrate. The substrate was ultrasonically washed with acetone and isopropyl alcohol (IPA) in order, washed by boiling in IPA, and then dried. Further, the substrate was washed with UV/ozone and used as the transparent conductive support substrate.

A chloroform solution of a compound represented by compound 10 was deposited to a thickness of 30 nm on the transparent conductive support substrate by spin coating to form a hole injection layer.

Further, organic layers and electrode layers described below were continuously formed by resistance-heating vacuum evaporation in a vacuum chamber of $10^{-5}$ Pa to produce an element.

Hole transport layer (20 nm): compound 10

Light-emitting layer (40 nm): exemplified compound 1-1 (concentration by weight: 10%); compound 11 (concentration by weight: 90%)

Electron transport layer (30 nm): compound 12

Metal electrode layer 1 (0.5 nm): LiF

Metal electrode layer 2 (150 nm): Al

The structural formulae of compounds 10, 11, and 12 are shown below.

[Chem. 22]

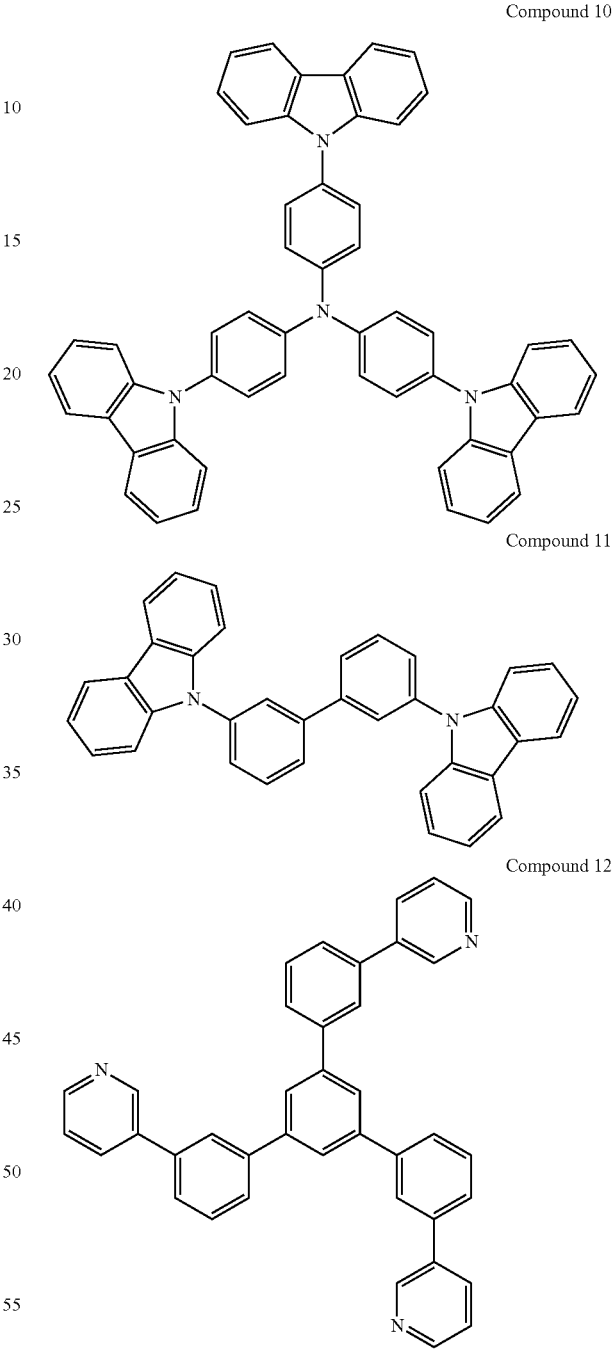

The characteristics of the resulting organic light-emitting element were measured and evaluated. Specifically, the current-voltage characteristics of the element were measured with microammeter 4140B manufactured by Hewlett-Packard Company, and the emission luminance of the element was measured with BM7 manufactured by Topcon Corporation. The organic light-emitting element showed blue light emission of x=0.19 and y=0.34 in the CIE standard color system at an emission luminance of 1000 cd/m$^2$ and also showed a luminous efficiency of 18.4 cd/A and an external quantum yield of 8.4%. Further, when a voltage was applied to the element for 100 hours in a nitrogen atmosphere, good continuous light emission was confirmed.

Therefore, an iridium complex according to the present invention is a novel compound having high quantum yield and emission suitable for blue color and capable of producing a light-emitting element having good emission characteristics when used for an organic light-emitting element.

As described above by giving the embodiments and the examples, the present invention can provide an iridium complex which is excellent in blue light emission characteristics. Also, the invention can provide an organic light-emitting element having excellent emission characteristics.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-278969, filed Dec. 8, 2009, which is hereby incorporated by reference herein in its entirety.

The invention claimed is:

1. An iridium complex represented by the following general formula (1):

[Chem. 1]

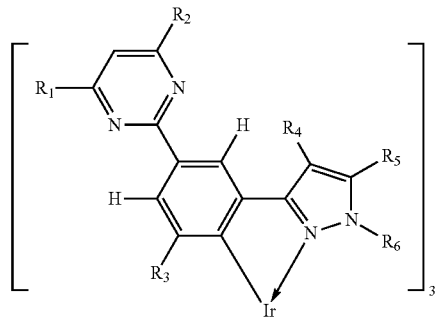

(1)

wherein $R_1$ and $R_2$ are each independently selected from a tertiary butyl group, an adamantyl group, and a bicyclooctyl group, $R_3$ is selected from a hydrogen atom, a halogen atom, and a cyano group, $R_4$ and $R_5$ are each independently selected from a hydrogen atom, a halogen atom, a cyano group, an alkyl group, an alkoxy group, and an amino group, and $R_6$ is an alkyl group.

2. The iridium complex according to claim 1, wherein both the $R_1$ and $R_2$ are tertiary butyl groups.

3. The iridium complex according to claim 1, wherein the $R_6$ is a methyl group.

4. The iridium complex according to claim 1, wherein the iridium complex emits blue light.

5. A material for an organic light-emitting element comprising the iridium complex according to claim 1.

6. An organic light-emitting element comprising a pair of electrodes and an organic compound layer disposed between the pair of electrodes,
wherein the organic compound layer contains the iridium complex according to claim 1.

7. The organic light-emitting element according to claim 6, wherein the organic compound layer is a light-emitting layer, the light-emitting layer includes a host material and a guest material, and the guest material contains the iridium complex.

8. A display device comprising a plurality of pixels, each of the pixels including the organic light-emitting element according to claim 6 and a switching element connected to the organic light-emitting element.

9. An illuminating device comprising the organic light-emitting element according to claim 6.

10. An electrophotographic image forming apparatus comprising an exposure light source, wherein the exposure light source comprises the organic light-emitting element according to claim 6.

11. An exposure light source of an electrophotographic image forming apparatus comprising the organic light-emitting element according to claim 6.

* * * * *